United States Patent
Dado et al.

(10) Patent No.: US 10,315,988 B2
(45) Date of Patent: Jun. 11, 2019

(54) ALPHA-OLEFIN SULFONIC DIMER ACID PROCESS

(71) Applicant: STEPAN COMPANY, Northfield, IL (US)

(72) Inventors: Gregory P. Dado, Chicago, IL (US); Aaron Sanders, Chicago, IL (US); Xue Min Dong, Lincolnshire, IL (US); E. Carolina Rojas, Highland Park, IL (US)

(73) Assignee: STEPAN COMPANY, Northfield, IL (US)

( * ) Notice: Subject to any disclaimer, the term of this patent is extended or adjusted under 35 U.S.C. 154(b) by 0 days.

(21) Appl. No.: 15/749,798

(22) PCT Filed: Jul. 28, 2016

(86) PCT No.: PCT/US2016/044375
§ 371 (c)(1),
(2) Date: Feb. 2, 2018

(87) PCT Pub. No.: WO2017/023664
PCT Pub. Date: Feb. 9, 2017

(65) Prior Publication Data
US 2018/0222854 A1   Aug. 9, 2018

Related U.S. Application Data

(60) Provisional application No. 62/200,969, filed on Aug. 4, 2015.

(51) Int. Cl.
| | |
|---|---|
| *C09K 8/02* | (2006.01) |
| *C09K 8/94* | (2006.01) |
| *C07G 99/00* | (2009.01) |
| *C07C 303/06* | (2006.01) |
| *C07C 303/22* | (2006.01) |
| *C07C 309/04* | (2006.01) |
| *C07C 309/05* | (2006.01) |
| *C07C 309/20* | (2006.01) |
| *C07C 309/62* | (2006.01) |

(52) U.S. Cl.
CPC .......... *C07C 303/06* (2013.01); *C07C 303/22* (2013.01); *C07C 309/05* (2013.01); *C07C 309/62* (2013.01); *C07G 17/004* (2013.01); *C09K 8/02* (2013.01); *C09K 8/94* (2013.01)

(58) Field of Classification Search
None
See application file for complete search history.

(56) References Cited

U.S. PATENT DOCUMENTS

| | | | |
|---|---|---|---|
| 3,721,707 A | 3/1973 | Straus et al. | |
| 3,873,590 A * | 3/1975 | Straus .................. | C07G 17/002 510/426 |
| 3,951,823 A | 4/1976 | Straus et al. | |
| 3,953,338 A | 4/1976 | Straus et al. | |
| 4,059,620 A | 11/1977 | Johnson et al. | |
| 4,556,107 A | 12/1985 | Duerksen et al. | |
| 4,567,232 A | 1/1986 | Echte et al. | |
| 4,607,700 A | 8/1986 | Duerksen et al. | |
| 4,957,646 A | 9/1990 | Borchardt et al. | |
| 5,052,487 A | 10/1991 | Wall | |
| 5,279,367 A | 1/1994 | Osterloh | |
| 6,043,391 A | 3/2000 | Berger et al. | |
| 2018/0223173 A1 * | 8/2018 | Rojas ..................... | C09K 8/592 |

FOREIGN PATENT DOCUMENTS

| | | |
|---|---|---|
| EP | 0446971 B1 | 7/1994 |
| GB | 2284601 A | 6/1995 |

OTHER PUBLICATIONS

PCT International Search Report and Written Opinion dated Sep. 28, 2016 from corresponding Application No. PCT/US2016/044375, 11 pages.

* cited by examiner

*Primary Examiner* — Amy C Bonaparte
(74) *Attorney, Agent, or Firm* — Dilworth IP, LLC

(57) ABSTRACT

Methods of making an alpha-olefin sulfonic dimer acid (AOS dimer acid) are disclosed. In one method, an alpha-olefin is sulfonated, preferably with sulfur trioxide, to produce a mixture comprising an alpha-olefin sulfonic acid (AOS acid) and sulfur dioxide. This mixture is then heated while purging sulfur dioxide and hydrogen sulfide from the reactor to produce an AOS dimer acid composition. In another method, the AOS acid mixture is treated to remove sulfur dioxide and is then heated to produce an AOS dimer acid composition. With either method, the resulting AOS dimer acid composition has at least a 30% decrease in the level of elemental sulfur when compared with that of an AOS dimer acid composition prepared by a similar process in the absence of any active removal of sulfur dioxide or hydrogen sulfide. AOS dimer acid compositions and salts of the AOS dimer acids, which are useful surfactants for oilfield and other applications, are also disclosed.

24 Claims, No Drawings

ALPHA-OLEFIN SULFONIC DIMER ACID PROCESS

FIELD OF THE INVENTION

The invention relates to alpha-olefin sulfonic dimer acids and a process for making them. Salts of the dimer acids are useful surfactants for oilfield chemical and other applications.

BACKGROUND OF THE INVENTION

Oilfield chemical applications require robust surfactants that can provide good foaming at elevated temperatures and/or pressures. Suitable surfactants for this purpose include salts of alpha-olefin sulfonic dimer acid ("AOS dimer acid," see, e.g., U.S. Pat. Nos. 4,556,107; 4,567,232; 4,607,700; 4,957,646; and 5,052,487). Dilute blends of alpha-olefin sulfonates and unsaturated fatty acids (e.g., oleic acid) have been used as steam foaming agents (see, e.g., U.S. Pat. No. 5,279,367).

Dimerization of alpha-olefin sulfonic acid (AOS acid) is described, for example, in U.S. Pat. Nos. 3,721,707 and 3,951,823. Briefly, AOS acid produced by sulfonation of one or more alpha-olefins, is heated at 110° C. to 200° C. to induce oligomerization. Under these conditions, intermediate sultones and alkene sulfonic acids are converted to alkane sulfonic acids and other products. The molecular weight of the product is roughly double that of the AOS acid, and hence the term "AOS dimer acid" to describe it. However, the structure of the product can be rather complex, as illustrated in the '707 patent.

In practice, dimerization of AOS acid is complicated by the formation of undesirable by-products, particularly hydrogen sulfide and elemental sulfur. Correspondingly, the sulfonic acid content of the AOS dimer acid is substantially lower than the theoretical amount based on the molecular weight of the olefin and the $SO_3$ stoichiometry used to produce the AOS acid. For instance, when a 65:35 (wt./wt.) mixture of $C_{14}/C_{16}$ alpha-olefins is sulfonated with a 5% molar excess of $SO_3$ by falling-film sulfonation, and the AOS acid is dimerized according to known methods, the resulting AOS dimer acid typically contains 2.9-3.4 meq/g of sulfonic acid content instead of a theoretical yield of 3.62 meq/g. The problems of low sulfonic acid content and generation of reduced sulfur compounds apparently have not been previously recognized or addressed.

Hydrogen sulfide is highly toxic, has a relatively low explosive limit in air, and has an offensive odor. Elemental sulfur sublimes and can deposit onto reactor and pipe surfaces, leading to equipment fouling during production and use of AOS dimer acid. Neutralization of AOS dimer acid can convert hydrogen sulfide to sodium sulfide ($Na_2S$); however, this material can become a safety hazard later when the neutralized AOS dimer acid is acidified and $H_2S$ is liberated. It is therefore highly desirable to minimize or eliminate hydrogen sulfide and elemental sulfur during the production of AOS dimer acid.

AOS acids, upon aging, will generate some sulfur dioxide. Moreover, when AOS acids are heated to produce AOS dimer acids, the sulfur dioxide content can increase dramatically. The presence of $SO_2$ is easily confirmed by Dräger tube analysis of the reactor headspace during AOS acid dimerization. Although prior-art processes for making AOS dimer acid generally ignore any increased generation of sulfur dioxide, we believe sulfur dioxide can be reduced to elemental sulfur, most likely via a reaction with hydrogen sulfide. Consequently, removal of sulfur dioxide and/or hydrogen sulfide during AOS dimer production merits due consideration.

The oilfield chemicals industry would benefit from improved AOS dimer acids and their salts and ways to produce them. The AOS dimer acid salts are surfactants with desirable elevated temperature foaming character. Especially needed are methods that would afford AOS dimer acids with a reduced level of undesirable by-products, particularly hydrogen sulfide and elemental sulfur. Ideally, the methods could be easily implemented without a need for substantial capital investment.

SUMMARY OF THE INVENTION

In one aspect, the invention relates to a method of making an alpha-olefin sulfonic dimer acid ("AOS dimer acid"). The method comprises two steps. First, an alpha-olefin is sulfonated, preferably with sulfur trioxide, to produce a mixture comprising an alpha-olefin sulfonic acid ("AOS acid") and sulfur dioxide. The mixture from this first step is then heated in a reactor at a temperature within the range of 110° C. to 200° C. while purging sulfur dioxide and hydrogen sulfide from the reactor to produce an AOS dimer acid composition.

In a second method, an alpha-olefin is sulfonated, preferably with sulfur trioxide, to produce a mixture comprising an AOS acid and sulfur dioxide, and sulfur dioxide is then removed from this mixture, preferably by digesting, vacuum stripping, gas purging, solvent-assisted stripping, heating, or a combination thereof. The reaction mixture is then heated in a reactor at a temperature within the range of 110° C. to 200° C. to produce an AOS dimer acid composition.

With each method, we surprisingly found that the resulting AOS dimer acid composition has at least a 30% decrease in the level of elemental sulfur when compared with that of an AOS dimer acid composition prepared by a similar process in the absence of any active removal of sulfur dioxide or hydrogen sulfide.

Without wishing to be bound by any particular theory, we believe that sulfur dioxide and hydrogen sulfide, which are generated in substantial quantities during AOS acid dimerization, react to form elemental sulfur and water ($SO_2+2H_2S \rightarrow 3S+2H_2O$).

The methods provide AOS dimer acid products with reduced amounts of hydrogen sulfide and elemental sulfur in the product, and when desired, enhanced sulfonic acid functionality. Thus, the invention includes AOS dimer acid compositions made by the methods described above and salts of the AOS dimer acids.

In other aspects, the invention relates to compositions comprising a dimer acid prepared from a $C_5$-$C_{50}$ AOS acid. The compositions have less than 5 mole % of elemental sulfur.

Salts of the AOS dimer acids are useful surfactants for oilfield chemical and other applications, especially high-temperature applications.

DETAILED DESCRIPTION OF THE INVENTION

Methods for producing AOS dimer acid compositions having reduced levels of elemental sulfur are described in more detail below. In each case, the amount of elemental sulfur present in the product is at least 30% less than that found in products made using a comparable benchmark method.

I. First Method

A first aspect of the invention relates to a two-step method of making an alpha-olefin sulfonic dimer acid ("AOS dimer acid"). First, an alpha-olefin is sulfonated, preferably with sulfur trioxide, to produce a mixture comprising an alpha-olefin sulfonic acid (AOS acid) and sulfur dioxide. This mixture is then heated while purging sulfur dioxide and hydrogen sulfide from the reactor to produce an AOS dimer acid composition.

A. Alpha-Olefin Sulfonation

Suitable alpha-olefins have a $C_5$ to $C_{50}$ linear or branched carbon chain and a terminal carbon-carbon double bond. Preferred alpha-olefins for use herein will provide, upon sulfonation and dimerization, AOS dimer acids whose salts have good foaming qualities and adequate thermal stability for use in oilfield applications. The alpha-olefins may comprise, for example, $C_8$ to $C_{40}$ alpha-olefins, $C_{10}$ to $C_{30}$ alpha-olefins, $C_{12}$ to $C_{18}$ alpha-olefins, $C_{14}$ to $C_{16}$ alpha-olefins, $C_{20}$ to $C_{24}$ alpha-olefins, $C_{26}$ to $C_{28}$ alpha-olefins, or combinations thereof.

Any method suitable for sulfonating alpha-olefins can be used to produce the AOS acid. In general, any method for converting alpha-olefins to hydroxyalkane sulfonic acids, sultones, alkene sulfonic acids, or mixtures thereof, may be used. Analysis of the crude sulfonic acid product normally shows the presence of 1,3- and 1,4-sultones, hydroxyalkane sulfonic acids, and alkene sulfonic acids. Thus, as used herein, "AOS acid" usually refers to a mixture of monomeric compounds, at least some of which have sulfonic acid functionality. Sulfonation with sulfur trioxide is preferred. For more examples of suitable alpha-olefin sulfonation processes, see U.S. Pat. Nos. 3,951,823; 4,556,107; 4,567,232; 4,607,700; and 4,957,646, the teachings of which are incorporated herein by reference.

Methods for sulfonating alpha-olefins with sulfur trioxide to generate alpha-olefin sulfonic acids are well known. One exemplary procedure is shown in U.S. Pat. No. 3,721,707, the teachings of which are incorporated herein by reference. Briefly, an alpha-olefin or mixture of alpha-olefins is introduced into a falling-film reactor along with a diluted mixture of sulfur trioxide and a diluent gas, which may be air or nitrogen, for example. A volatile solvent such as hexane or dioxane can be used as a diluent if desired. The reaction temperature is conveniently maintained within a desired range, for example, 40° C. to 70° C., by means of external cooling, and the product is kept cold.

The degree of sulfonation ("DOS") used is a measure of the number of moles of sulfur trioxide used per mole of alpha-olefin reactant. The DOS can vary over a wide range depending on the desired outcome. In some cases, it will be desirable to use a relatively high DOS, such as at least 100% or 105%. In other cases, it may be more desirable to use a lower DOS, such as 20% to 40%, 50% to 70%, 75% to 95%, or the like. The DOS can be controlled through stoichiometry, reaction temperature, reaction time, sulfur trioxide concentration, flow rates, equipment selection, and other factors that are within the skilled person's discretion.

Within the context of AOS acid dimerization processes, the amounts of sulfur dioxide and hydrogen sulfide generated have been, until now, overlooked. Through careful analysis of headspace, scrubber contents, and reaction products, we have been able to determine how much $SO_2$ and $H_2S$ are produced during AOS dimerization, what quantity of these "oxidizables" remains in the AOS dimer acid product, how much elemental sulfur is produced, and consequently, how to modify the process to minimize by-product generation and maximize the sulfonic acid content of the AOS dimer acid.

When the desired product is an olefin sulfonate salt from alpha-olefin sulfonation, the crude sulfonic acid product would normally be briefly digested at modest temperature, neutralized, and then subjected to hydrolysis of sultones with a small excess of caustic. However, when an AOS dimer acid is desired, as is the case here, the crude sulfonic acid product goes directly to a relatively high temperature dimerization (or "oligomerization") step without neutralization.

B. AOS Acid Dimerization with Hydrogen Sulfide/Sulfur Dioxide Purge

The crude sulfonic acid mixture produced as described above is "dimerized" by heating the mixture, preferably at a temperature within the range of 110° C. to 200° C., preferably 120° C. to 190° C., 130° C. to 170° C., or 140° C. to 160° C. Heating causes the sultone and sulfonic acid products to dimerize, thereby producing a complex mixture of products having a molecular weight that is approximately double that of the original feed. In the course of dimerization, the population of sultones and alkene sulfonic acids diminishes such that the final product is substantially depleted or is free of sultones and alkene sulfonic acids. As shown in U.S. Pat. No. 3,721,707, the resulting sulfonic acid dimers can be aliphatic, cycloaliphatic, and even aromatic in character when head-to-head or head-to-tail dimers form. In addition to the desired disulfonated dimers, the mixture may include monosulfonated monomers, monosulfonated dimers, and other products. The product mixture thus obtained is referred to herein as "AOS dimer acid."

Heating to dimerize the AOS acid normally continues until the dimerization is reasonably complete, e.g., at least 95%. However, it may be desirable in some cases to perform the dimerization under conditions effective to achieve only partial conversion of the AOS acid. Thus, in some aspects, the % conversion of AOS acid to AOS dimer acid composition is maintained within the range of 20 to 90%, in some aspects 50 to 90%, and in some aspects 75 to 90%. One convenient method of measuring conversion is to analyze the AOS dimer acid composition by $^1$H NMR spectroscopy using an internal standard such as isopropyl myristate, wherein the sum total meq/g of unreacted sultones and alkene sulfonic acids can be quantified, and wherein the % conversion can then be derived from the difference between this total and the theoretical meq/g sulfonic acid that is based on the amount of sulfur trioxide used to make the AOS acid. The % conversion of AOS acid to AOS dimer acid can be controlled through reaction temperature, reaction time, flow rates, equipment selection, and other factors that are within the skilled person's discretion.

As noted in the background discussion, dimerization of AOS acid is complicated in practice by the formation of undesirable by-products, particularly hydrogen sulfide and elemental sulfur. One consequence is that the sulfonic acid content of the AOS dimer acid product is lower than would otherwise be desirable.

According to one aspect of the invention, the dimerization of AOS acid is performed in a reactor at a temperature within the range of 110° C. to 200° C. while purging sulfur dioxide and hydrogen sulfide from the reactor. Prior art descriptions of the process for making AOS dimer acid do not suggest active removal of sulfur dioxide or hydrogen sulfide from the dimerization reaction mixture (see, e.g., U.S. Pat. No. 3,721,707; heating at 150° C. for 2.25 h in a round-bottom flask with no purging of off-gases). We surprisingly found, however, that purging $SO_2$ and $H_2S$ from the reactor during dimerization provides an AOS dimer acid composition having at least a 30% decrease in the level of elemental sulfur compared with that of an AOS dimer acid composition prepared by a similar process in the absence of any active removal of sulfur dioxide or hydrogen sulfide.

Comparative Examples A and B, below, show that closed-reactor dimerizations of $C_{14}/C_{16}$ AOS acid under pressure (i.e., no purging) result in high headspace concentrations of hydrogen sulfide and relatively low ultimate sulfonic acid contents. Further, Comparative Examples C and D show that dimerizing AOS acid in glassware at atmospheric pressure, in the absence of any off-gas purging, quickly produces substantial hydrogen sulfide and elemental sulfur in the headspace under the conditions used to dimerize the AOS acid. Additionally, the sulfonic acid content of the product is lower than desirable.

Sulfur dioxide and/or hydrogen sulfide can be purged from the dimerization reactor by any suitable means. It is convenient, for instance, to sparge an inert gas such as nitrogen above and/or below the liquid surface in the reactor, and to recover the sulfur dioxide and/or hydrogen sulfide (hereinafter also called "oxidizables") in a scrubber containing aqueous base. Collecting the oxidizables in a scrubber enables quantification of these by-products by standard analytical methods, as is shown below in the examples.

Any desired flow rate for the sparge gas can be used, although there may be practical limits regarding the flow rate. As Examples 1 and 2 below demonstrate, a higher sparge rate may be more effective in eliminating sulfur dioxide and/or hydrogen sulfide, ultimately providing an AOS dimer acid having a higher sulfonic acid content. A desirable flow rate will depend on many factors, including the equipment involved, the mixing rate, the nature of the AOS acid reactant, the viscosity of the AOS dimer acid product, and other factors. In our experiments, a rate of about 1.5 mL/min/g of AOS acid provided excellent removal of sulfur dioxide and hydrogen sulfide (see Example 1), while a rate of about 0.1 mL/min/g of AOS acid was somewhat less effective (see Example 2).

Sulfur dioxide and hydrogen sulfide could also be purged during the dimerization process by other methods. For instance, one could continuously or periodically introduce a solvent along with or instead of an inert gas. Vacuum could also be applied to assist in the purging of these by-product gases.

The degree of success in removing sulfur dioxide and/or hydrogen sulfide can be assessed using the analytical methods described herein as well as other techniques that will occur to the skilled person. In general, measuring the amounts of by-products (sulfur dioxide, hydrogen sulfide, elemental sulfur) present in the AOS dimer acid composition, the amounts of off-gases (sulfur dioxide, hydrogen sulfide) collected in a scrubber, and the amount of sulfonic acid content in the AOS dimer acid composition help to quantify the degree of success of the purging method.

In particular, the AOS dimer acid composition produced in the inventive method has at least a 30% decrease, preferably at least a 50% decrease, in the level of elemental sulfur when compared with that of an AOS dimer acid composition prepared by a similar process in the absence of any active removal of sulfur dioxide or hydrogen sulfide. The content of elemental sulfur present in the sulfonic acid product can be determined as is described below in the section on analytical methods.

In some aspects, the AOS dimer acid composition may also have at least a 5% increase, preferably at least a 10% increase, in sulfonic acid content when compared with that of an AOS dimer acid composition prepared by a similar process in the absence of any active removal of sulfur dioxide or hydrogen sulfide. The sulfonic acid content is conveniently determined by potentiometric titration with an amine, as is described below.

In some aspects, the yield of sulfonic acid in the AOS dimer acid product is at least 85%, preferably at least 87%, of the theoretical amount. By "% yield," we mean a yield calculated based on the amount of sulfonic acid content (reported in milliequivalents of $SO_3$ per gram of AOS dimer acid product) actually measured in the AOS dimer acid product compared with the theoretical amount expected if all $SO_3$ used to prepare the AOS acid precursor were converted to sulfonic acid.

A non-limiting hypothetical calculation of % yield of sulfonic acid: Suppose an olefin feedstock of an equivalent weight of 200 g/mol was sulfonated with 1.05 molar equivalents of $SO_3$ (mol. wt.: 80.06 g/mol). The weight fraction of $SO_3$ used to prepare AOS acid would then be 0.296, and the theoretical amount of sulfonic acid expected in the AOS dimer acid product would be 3.70 meq/g. If the actually measured sulfonic acid content in the subsequently produced AOS dimer acid product was 3.35 meq/g, then the % yield of sulfonic acid would be 90.5%.

In some aspects, wherein the dimerization is performed in a manner effective to achieve only partial conversion, the % yield of sulfonic acid will comprise both the amount of sulfonic acid content actually measured in the AOS dimer acid product as well sultones, which do not analyze as sulfonic acids by titration but can be quantified by $^1H$ NMR spectroscopy or any other suitable method.

In other aspects, the AOS dimer acid composition contains less than 2.5 mole % of, preferably less than 2.0 mole % or less than 1.5 mole % of by-product oxidizable components comprising hydrogen sulfide, sulfur dioxide, or mixtures thereof. Suppose, in the hypothetical illustration provided above, it was found that the product contained 0.10 meq/g of oxidizable by-products comprising hydrogen sulfide and sulfur dioxide. That product would then contain (0.10 meq/g/3.70 meq/g)×100=2.7 mole % of by-product oxidizable components.

In some aspects, the AOS dimer acid composition contains less than 5 mole %, preferably less than 4 mole % or less than 3 mole % of by-product elemental sulfur. Suppose, in the hypothetical illustration provided above, it was found that the product contained 0.050 meq/g of by-product elemental sulfur. That product would then contain (0.050 meq/g/3.70 meq/g)×100=1.35 mole % of by-product elemental sulfur.

In still other aspects, the method further comprises an additional step of removing sulfur dioxide from the AOS acid mixture produced in the first step (e.g., by digesting, vacuum stripping, gas purging, solvent-assisted stripping, heating, or a combination thereof) prior to performing the dimerization step. "Digesting" may involve a soak period, preferably with added heat, to liberate sulfur dioxide from the AOS acid mixture.

In some aspects, the method further comprises treating the AOS dimer acid composition with an oxidizing agent (e.g., hydrogen peroxide) to destroy hydrogen sulfide.

Examples 1-3 below illustrate the first method.

II. Second Method

In another aspect, an alpha-olefin is sulfonated, preferably with sulfur trioxide, to produce a mixture comprising an AOS acid and sulfur dioxide, and sulfur dioxide is then removed from this mixture. The treated AOS acid is then heated in a reactor at a temperature within the range of 110° C. to 200° C. to produce an AOS dimer acid composition.

A. Alpha-Olefin Sulfonation

Sulfonation of the alpha-olefin to give an AOS acid product is performed as described earlier for the First Method.

B. Removal of Sulfur Dioxide Prior to AOS Acid Dimerization

In the second step of this Second Method, sulfur dioxide is removed from the AOS acid (i.e., the product of sulfonating the alpha-olefin) prior to dimerization.

Removal of sulfur dioxide can be performed by any desired method. Preferably, sulfur dioxide removal is performed by digesting, vacuum stripping, gas purging, solvent-assisted stripping, heating, or a combination thereof.

"Digesting" may refer to a soak period during which sulfur dioxide is allowed to evolve from a warm AOS acid product, or it may refer to a period during which the AOS acid is warmed or heated to promote sulfur dioxide evolution. In some aspects, a digestion step may precede or follow other sulfur dioxide removal methods.

When vacuum stripping is used, the amount of vacuum applied should be sufficient to remove sulfur dioxide from the reactor while also being insufficient to remove AOS acid or sultone intermediates from the reactor. The degree of vacuum that can be applied will depend on the molecular weight of the AOS acid, temperature, equipment, whether or not a solvent is included, whether or not a gas purge is used, and other factors within the skilled person's discretion. In some cases, it may be convenient to use a wiped-film evaporator for vacuum stripping. Wiped-film evaporation can be performed at relatively high temperatures (e.g., 130° C. or higher) with short residence times. This allows removal of sulfur dioxide from the AOS acid without generating significant levels of hydrogen sulfide or elemental sulfur.

Gas purging can be used alone or in combination with other sulfur dioxide removal techniques. Air or inert gases such as nitrogen or argon can be used for purging. The purge should be performed under conditions sufficient to remove most or all of the sulfur dioxide present in the AOS acid prior to the dimerization step.

Solvent-assisted stripping can be used alone or in combination with gas purging and/or vacuum stripping. A volatile hydrocarbon solvent such as petroleum ether works well for this purpose.

Heating may accompany any of the earlier-described techniques, provided that the amount of heat is insufficient to induce a significant degree of dimerization. Typically, when heat is added, the temperature will be held within the range of 40° C. to 140° C., preferably 50° C. to 130° C.

Example 4 below illustrates the combination of heating and gas purging to remove sulfur dioxide prior to dimerization of the AOS acid. Examples 5 and 6 illustrate the combination of solvent stripping, heating, and vacuum stripping (using petroleum ether and a rotary evaporator) to remove sulfur dioxide from an AOS acid prior to dimerization.

For any of the sulfur dioxide removal methods or their combinations, the degree of success can be evaluated by measuring the amount of oxidizables (i.e., sulfur dioxide, hydrogen sulfide) present in a scrubbing device, solvent mixture, or other source of removed by-product gases using the analytical methods described below or other suitable analytical tools.

C. AOS Acid Dimerization

The alpha-olefin sulfonic acid product, after removal of sulfur dioxide as described above, is dimerized as previously described for the First Method by heating at a temperature within the range of 110° C. to 200° C., preferably 120° C. to 190° C., 130° C. to 170° C., or 140° C. to 160° C.

The resulting AOS dimer acid composition produced has at least a 30% decrease, preferably at least a 50% decrease, in the level of elemental sulfur when compared with that of an AOS dimer acid composition prepared by a similar process in the absence of any active removal of sulfur dioxide or hydrogen sulfide.

In some aspects, the AOS dimer acid composition contains less than 5 mole %, preferably less than 4 mole % or less than 3 mole % of by-product elemental sulfur.

In some aspects, the AOS dimer acid composition may have at least a 5% increase, preferably at least a 10% increase, in sulfonic acid content when compared with that of an AOS dimer acid composition prepared by a similar process in the absence of any active removal of sulfur dioxide or hydrogen sulfide.

In some aspects, the yield of AOS dimer acid is at least 85%, preferably at least 87%, of the theoretical amount.

In other aspects, the AOS dimer acid composition contains less than 2.5 mole % of, preferably less than 2.0 mole % or less than 1.5 mole % of by-product oxidizable components comprising hydrogen sulfide, sulfur dioxide, or mixtures thereof.

In other aspects, the reactor is sealed during the dimerization step. Example 5 below illustrates this aspect.

In other aspects, the method further comprises purging hydrogen sulfide and sulfur dioxide from the reactor during the dimerization step. Example 6 below illustrates this aspect.

In still other aspects, the method further comprises an additional step of treating the AOS dimer acid composition with an oxidizing agent to destroy hydrogen sulfide.

III. AOS Dimer Acid Compositions and Salts Therefrom

In another aspect, the invention relates to AOS dimer acid compositions made by the methods described hereinabove. The compositions differ from known AOS dimer compositions. Compared with compositions made by other known processes, the inventive AOS dimer compositions have at least a 30% decrease, preferably at least a 50% decrease, in the level of elemental sulfur.

In some aspects, the compositions have at least a 5% increase, preferably at least a 10% increase, in sulfonic acid content when compared with compositions made by known processes that do not actively remove sulfur dioxide during preparation.

Another inventive composition comprises a dimer acid prepared from a $C_5$-$C_{50}$ AOS acid, preferably a $C_{14}$-$C_{30}$ AOS acid, wherein the composition has less than 5 mole % of by-product elemental sulfur.

The invention includes salts made by neutralizing any of the AOS dimer acid compositions mentioned above with an effective amount of a base, preferably an alkali metal hydroxide, alkaline earth metal hydroxide, ammonia, or an alkylammonium compound. The salts are useful surfactants for oilfield and other applications.

The salts may also be useful as surfactants for hard or soft surface cleaning, laundry detergents, personal care applications, enhanced oil recovery, oil dispersants, agricultural applications, emulsion polymers, metalworking, industrial applications, specialty foamers, and the like.

The following examples merely illustrate the invention; those skilled in the art will recognize many variations that are within the spirit of the invention and scope of the claims.

Analytical Methods:

Headspace Analysis

Sulfur dioxide and hydrogen sulfide in reactor headspace is determined by means of Dräger gas analysis tubes. A single stroke with a handpump (Accuro, Drager Safety Inc.) is used to draw reaction headspace gas into the analysis tubes. For $H_2S$ analyses, 0.2%/A tubes are used, with an estimated lower detection limit of about 500 ppm. For $SO_2$ analyses, 50/b tubes are used, with an estimated lower detection limit of about 50 ppm.

Sulfonic Acid Content of AOS Dimer Acid

Sulfonic acid content in AOS dimer acid products is measured by potentiometric titration with 0.1 N cyclohexylamine in methanol.

Total Volatile Oxidizables

Total volatile oxidizables stripped from reaction mixtures and captured by aqueous caustic scrubbing are quantified by the following titration method: A precise volume (typically 1.00 or 2.00 mL) of 0.1 N iodine solution is added to ~0.2 N aqueous HCl. Scrubber liquid (1.00 mL) is added. Excess unreacted iodine is titrated with 0.01 N sodium thiosulfate using a platinum electrode to determine the potentiometric endpoint. The oxidizables, which comprise $SO_2$ and $H_2S$, are calculated (in meq/g, mol/g) recognizing that 1 mole of 12 reacts with 2 moles of sodium thiosulfate, 1 mole of 12 reacts with 1 mole of $H_2S$, and 1 mole of 12 reacts with 1 mole of $SO_2$. The total meq/g of oxidizables is calculated based on the mass of scrubber liquid. The amount of oxidizables stripped is calculated based on the original mass of AOS acid charged to the reactor, expressed in meq/g. Oxidizables in sulfonic acid and neutralized reaction products are measured by a comparable iodine/thiosulfate titration method.

Sulfur Analysis

Sulfur analyses (as elemental sulfur) are conducted by reaction of the sodium salts of reaction products, prepared by neutralization of sulfonic acid with NaOH in water, with a known amount of excess triphenylphosphine (TPP). The excess unreacted TPP is then titrated potentiometrically with iodine and the amount of elemental sulfur is calculated, based on the consumption of TPP and is reported in meq/g on a sulfonic acid basis.

Example 1

Preparation of AOS Dimer Acid with Removal of $SO_2$ and $H_2S$ Throughout the Reaction AOS acid is prepared by falling-film sulfonation of a 65/35 (wt./wt.) mixture of 1-tetradecene and 1-hexadecene in accordance with standard manufacturing practices. The degree of sulfonation is 1.05 moles of $SO_3$ per mole of olefin, which corresponds to 3.62 meq $SO_3$ per gram of AOS acid. The $C_{14}/C_{16}$ AOS acid (141 g) is charged to a 300-mL stainless-steel pressure reactor equipped with a nitrogen sparge tube that directs gas to the impeller zone of a mechanical stirrer. The stirrer is set to 350 rpm, and then a nitrogen flow of 200 mL/min. is established. The gas exits through an outlet that feeds a scrubber containing 250 g of aqueous caustic (7 g of NaOH). The contents of the reactor are heated to 150° C. over 1 h and are then maintained for 5 h. The nitrogen flow is discontinued and the reactor contents are allowed to cool to ambient temperature. $^1$H NMR analysis indicates complete conversion to AOS dimer acid products. Other analyses are summarized in Table 1.

TABLE 1

| | |
|---|---|
| Headspace $SO_2$ (ambient, end of reaction) | <50 ppm |
| Headspace $H_2S$ (ambient, end of reaction) | <500 ppm |
| Sulfonic acid in product | 3.24 meq/g |
| Yield of sulfonic acid in product | 89.5% |
| Oxidizables in product (as $SO_2$ and/or $H_2S$) | 0.03 meq/g |
| Mole % of by-product oxidizables in product | 0.8% |
| Elemental sulfur (on a sulfonic acid product basis) | 0.04 meq/g |
| Mole % of by-product elemental sulfur in product | 1.1% |
| % Decrease in elemental sulfur vs. Comparative Ex. B | 86.7% |
| Volatile oxidizables collected in scrubber (on starting AOS acid weight basis) | 0.37 meq/g |

The results of Example 1 demonstrate that a high, continuous nitrogen sparge rate maximizes $SO_2$ and $H_2S$ removal as it forms. The sulfonic acid content of the product is enhanced compared with products made by conventional processes that do not remove $SO_2$ or $H_2S$. Very little elemental sulfur is found in the sulfonic acid product.

Comparative Example A

Preparation of AOS Dimer Acid in a Closed Reactor, Inerted with $N_2$ $C_{14}/C_{16}$ AOS acid prepared in Example 1 (142 g) is charged to a 300-mL stainless-steel pressure reactor. Oxygen is purged from the reactor headspace by pressurizing the reactor with nitrogen, venting, repeating five times, then sealing the reactor after the final purge. The stirrer is set to 350 rpm. The reactor contents are heated to 150° C. over 1 h, maintained for 5 h, then allowed to cool to ambient temperature. $^1$H NMR analysis indicates complete conversion to AOS dimer acid products. Table A summarizes the results.

TABLE A

| | |
|---|---|
| Headspace $SO_2$ (ambient, end of reaction) | <50 ppm |
| Headspace $H_2S$ (ambient, end of reaction) | >80,000 ppm |
| Sulfonic acid in product | 3.00 meq/g |
| Yield of sulfonic acid in product | 82.9% |
| Oxidizables in product (as $SO_2$ and/or $H_2S$) | 0.11 meq/g |
| Mole % of by-product oxidizables in product | 3.0% |
| Elemental sulfur (on a sulfonic acid product basis) | 0.25 meq/g |
| Mole % of by-product elemental sulfur in product | 6.9% |

Compared with Example 1, the headspace of the reaction mixture, sampled directly from the reactor at ambient temperature and pressure, is extremely high in $H_2S$. In addition, the sulfonic acid content of the product is much lower, which indicates a substantially elevated level of reduced sulfur compound generation. Measured oxidizables in the product are elevated. Further, measured elemental sulfur in the sulfonic acid product increases six-fold compared with that of the product of Example 1.

Comparative Example B

Preparation of AOS Dimer Acid in a Closed Reactor, No Inertion

The stainless-steel pressure reactor is charged with $C_{14}/C_{16}$ AOS acid (140 g). The reactor is sealed, but no attempt is made to remove oxygen from the headspace. The stirrer is set to 350 rpm. The reactor contents are heated to 150° C.

over 1 h, maintained for 5 h, and then allowed to cool to ambient temperature. $^1$H NMR analysis indicates complete conversion to AOS dimer acid products. Analyses appear in Table B.

TABLE B

| | |
|---|---|
| Headspace SO$_2$ (ambient, end of reaction) | <50 ppm |
| Headspace H$_2$S (ambient, end of reaction) | >80,000 ppm |
| Sulfonic acid in product | 2.98 meq/g |
| Yield of sulfonic acid in product | 82.3% |
| Oxidizables in product (as SO$_2$ and/or H$_2$S) | 0.12 meq/g |
| Mole % of by-product oxidizables in product | 3.3% |
| Elemental sulfur (on a sulfonic acid product basis) | 0.30 meq/g |
| Mole % of by-product elemental sulfur in product | 8.3% |

When viewed with the results of Comparative Example A, the results in Table B demonstrate that incidental oxygen has no significant impact on the yield of sulfonic acid or the level of oxidizables in product acid. However, there is a further increase in the already-high level of elemental sulfur generation.

Example 2

Preparation of AOS Dimer Acid with Removal of SO$_2$ and H$_2$S Throughout the Reaction The procedure of Example 1 is repeated at a reduced nitrogen flow rate of 10 mL/min. $^1$H NMR analysis indicates complete conversion to AOS dimer acid products. Other analyses are summarized in Table 2.

TABLE 2

| | |
|---|---|
| Headspace SO$_2$ (ambient, end of reaction) | <50 ppm |
| Headspace H$_2$S (ambient, end of reaction) | 20,000 ppm |
| Sulfonic acid in product | 3.14 meq/g |
| Yield of sulfonic acid in product | 86.7% |
| Oxidizables in product (as SO$_2$ and/or H$_2$S) | 0.05 meq/g |
| Mole % of by-product oxidizables in product | 1.4% |
| Elemental sulfur (on a sulfonic acid product basis) | 0.12 meq/g |
| Mole % of by-product elemental sulfur in product | 3.3% |
| % Decrease in elemental sulfur vs. Comparative Ex. B | 60.2% |
| Volatile oxidizables collected in scrubber (on starting AOS acid weight basis) | 0.26 meq/g |

As shown in Table 2, reducing the flow rate of nitrogen results in an increase in headspace H$_2$S compared with Example 1. Additionally, the product has a sulfonic acid content that is intermediate between the values obtained in Example 1 and Comparative Examples A and B. Elemental sulfur is also intermediate between the values observed in Example 1 and the comparative examples.

Comparative Examples C and D

Preparation of AOS Dimer Acid in a Reaction Open to Atmosphere

C$_{14}$/C$_{16}$ AOS acid (400 g) is charged to a 1-L round-bottom flask equipped with an overhead mechanical stirrer. No provision for blanketing with inert gas or sweeping of reaction headspace is provided. The AOS acid is heated, and the reaction progress is monitored by titration of aliquots with cyclohexylamine in methanol. Condensation of liquid droplets is observed in the relatively cool headspace of the reactor. Initially, the droplets appear colorless and transparent, then milky-white, then bright yellow due to sublimation of elemental sulfur. When the sulfonic acid content of the reaction product becomes constant, the reaction is judged complete, and the contents are allowed to cool to ambient temperature. Table C/D summarizes the results. In addition, a Drager tube analysis in Comparative Example D, conducted at the end of the reaction and at ambient temperature, indicates 80,000 ppm of headspace hydrogen sulfide.

TABLE C/D

| | Comparative Example | |
|---|---|---|
| | C | D |
| Reaction temperature | 130° C. | 150° C. |
| Reaction time | 16 h | 3.5 h |
| Onset of yellow appearance in headspace | 2.5 h | 1.2 h |
| Sulfonic acid in product | 3.02 meq/g | 3.07 meq/g |
| Yield of sulfonic acid in product | 83.4% | 84.8% |
| Oxidizables in product (as SO$_2$ and/or H$_2$S) | 0.11 meq/g | 0.13 meq/g |
| Mole % of by-product oxidizables in product | 3.0% | 3.6% |

These experiments mimic a known process for making AOS dimer, i.e., reaction at 130° C. or 150° C. with an open atmosphere and no intentional removal of SO$_2$ or H$_2$S as they form (see, e.g., U.S. Pat. No. 3,721,707). High elemental sulfur is evident from inspection of the reactor headspace. As shown in the table, the sulfonic acid content and oxidizables in the reaction products are comparable to those described in Comparative Examples A and B.

Example 3

Preparation of AOS Dimer Acid at 130° C. with Removal of SO$_2$ and H$_2$S Throughout the Reaction Example 2 is repeated utilizing a submerged nitrogen sparge of 10 mL/min throughout the reaction, but with a lower reaction temperature (130° C.) and an extended reaction time (13 h). $^1$H NMR analysis indicates complete conversion to AOS dimer acid products. Other analyses are summarized in Table 3.

TABLE 3

| | |
|---|---|
| Headspace SO$_2$ (ambient, end of reaction) | <50 ppm |
| Headspace H$_2$S (ambient, end of reaction) | 5000 ppm |
| Sulfonic acid in product | 3.16 meq/g |
| Yield of sulfonic acid in product | 87.3% |
| Oxidizables in product (as SO$_2$ and/or H$_2$S) | 0.07 meq/g |
| Mole % of by-product oxidizables in product | 1.9% |
| Elemental sulfur (on a sulfonic acid product basis) | 0.12 meq/g |
| Mole % of by-product elemental sulfur in product | 3.3% |
| % Decrease in elemental sulfur vs. Comparative Ex. B | 60.2% |
| Volatile oxidizables collected in scrubber (on starting AOS acid weight basis) | 0.34 meq/g |

The sulfonic acid content of the AOS dimer acid and the oxidizables and elemental sulfur in the obtained product are similar to that of Example 2.

Example 4

Preparation of AOS Dimer Acid with Removal of SO$_2$ Prior to Dimerization (Closed Reactor)

C$_{14}$/C$_{16}$ AOS acid (141 g) is charged to a 300-mL stainless-steel pressure reactor equipped with a nitrogen sparge tube that directs gas to the impeller zone of a mechanical stirrer. The reactor is sealed and the stirrer is set to 350 rpm. A nitrogen sparge of 100 mL/min. is established. The gas exits through an outlet that feeds a scrubber containing 250 g of aqueous caustic (7 g of NaOH). The contents of the reactor are heated to 120° C. over 0.5 h and are then maintained for 5 h. The nitrogen flow is discontinued, the reactor is sealed, and the contents are heated to 150° C. and held for 5 h. $^1$H NMR analysis indicates complete conversion to AOS dimer acid products. Other analyses are summarized in Table 4.

TABLE 4

| | |
|---|---|
| Sulfonic acid in product | 3.12 meq/g |
| Yield of sulfonic acid in product | 86.2% |
| Oxidizables in product (as SO$_2$ and/or H$_2$S) | 0.09 meq/g |
| Mole % of by-product oxidizables in product | 2.5% |
| Elemental sulfur (on a sulfonic acid product basis) | 0.07 meq/g |
| Mole % of by-product elemental sulfur in product | 1.9% |
| % Decrease in elemental sulfur vs. Comparative Ex. B | 77.1% |
| Volatile oxidizables collected in scrubber (on starting AOS acid weight basis) | 0.30 meq/g |

The results demonstrate that pre-dimerization sparging with nitrogen effectively removes SO$_2$, resulting in a much lower elemental sulfur level in the product and somewhat higher sulfonic acid content in the AOS dimer acid when compared with the sealed reactor experiments in Comparative Examples A and B.

Example 5

Preparation of AOS Dimer Acid with Pre-Stripped AOS Acid, Subsequent Closed Reaction C$_{14}$/C$_{16}$ AOS acid is heated to 120° C. with stirring in a round-bottom flask for 2 h. Sulfur dioxide is then stripped from the acid sample via rotary evaporation under vacuum at 60° C. using multiple portions of petroleum ether to assist in the removal of off-gas. The stripped AOS acid (143 g) is charged to a 300-mL stainless-steel pressure reactor equipped with a mechanical stirrer. The reactor is sealed, the stirrer is set to 350 rpm, and the contents are heated to 150° C. and held for 5 h. $^1$H NMR analysis indicates complete conversion to AOS dimer acid products. Other analyses are summarized in Table 5.

TABLE 5

| | |
|---|---|
| Sulfonic acid in product | 3.09 meq/g |
| Yield of sulfonic acid in product | 85.4% |
| Oxidizables in product (as SO$_2$ and/or H$_2$S) | 0.09 meq/g |
| Mole % of by-product oxidizables in product | 2.5% |
| Elemental sulfur (on a sulfonic acid product basis) | 0.08 meq/g |
| % Decrease in elemental sulfur vs. Comparative Ex. B | 73.5% |
| Mole % of by-product elemental sulfur in product | 2.2% |

The results demonstrate that digestion of AOS acid at 120° C. followed by stripping to remove sulfur dioxide is an effective pre-treatment technique. The resulting AOS acid, upon dimerization in a closed reactor, gives an AOS dimer acid product with low oxidizables, a low elemental sulfur content, and an elevated sulfonic acid content compared with products from other sealed reactor experiments that do not use the pre-treatment, such as Comparative Example A.

Example 6

Preparation of AOS Dimer Acid with Pre-Stripped AOS Acid and Subsequent Reaction with Continuous N$_2$ Sparge Example 5 is repeated, but instead of conducting the 150° C. dimerization reaction in a closed reactor, a continuous nitrogen sparge of 10 mL/min is used. $^1$H NMR analysis indicates complete conversion to AOS dimer acid products. Other analyses are summarized in Table 6.

TABLE 6

| | |
|---|---|
| Sulfonic acid in product | 3.12 meq/g |
| Yield of sulfonic acid in product | 86.1% |
| Oxidizables in product (as SO$_2$ and/or H$_2$S) | 0.04 meq/g |
| Mole % of by-product oxidizables in product | 1.1% |
| Elemental sulfur (on a sulfonic acid product basis) | not detected |
| % Decrease in elemental sulfur vs. Comparative Ex. B | 100% |
| Mole % of by-product elemental sulfur in product | not detected |

The results show that pre-treatment of the AOS acid coupled with sparging during the dimerization produces a product with improved sulfonic acid content and very low oxidizables and elemental sulfur.

Comparative Example E

Demonstration that Pre-Treatment of AOS Acid with H$_2$O$_2$ is not Effective in Enabling a Dimerized Acid Product with Increased Sulfonic Acid Content C$_{14}$/C$_{16}$ AOS acid (150 g) is charged to a 500-mL round-bottom flask equipped with magnetic stir bar. The acid is heated to 130° C. for 0.5 h, resulting in an increase in oxidizables from 0.07 meq/g to 0.23 meq/g. Upon cooling, water (0.52 g) and then 35% H$_2$O$_2$ (5.19 g) are added, resulting in an exotherm to about 70° C. The amount of peroxide used corresponds to 0.23 meq/g on an acid basis. Upon cooling, the oxidizables content is found to be 0.051 meq/g. The acid is then re-heated to 100° C. for 2 h, and then 130° C. for 2 h. The oxidizables content is measured as 0.15 meq/g. The acid is cooled and transferred to a 300-mL stainless-steel pressure reactor. Upon sealing, the reaction mixture is maintained at 150° C. for 7 h. The product comprises 2.83 meq/g sulfonic acid (78.2% yield).

The result indicates that pre-treatment of AOS acid with hydrogen peroxide is ineffective in preventing subsequent generation of high levels of SO$_2$ upon heating the AOS acid for the purpose of dimerization. Moreover, the sulfonic acid content of the resulting AOS dimer acid is relatively very low.

The preceding examples are meant only as illustrations; the following claims define the invention.

We claim:
1. A method which comprises:
    (a) sulfonating an alpha-olefin to produce a mixture comprising an alpha-olefin sulfonic acid (AOS acid) and sulfur dioxide;
    (b) heating the mixture from step (a) in a reactor at a temperature within the range of 110° C. to 200° C. while purging sulfur dioxide and hydrogen sulfide from the reactor to produce an AOS dimer acid composition; wherein the AOS dimer acid composition has at least a 30% decrease in the level of elemental sulfur when compared with that of an AOS dimer acid composition prepared by the same process in the absence of any active removal of sulfur dioxide or hydrogen sulfide.
2. The method of claim 1 wherein the AOS dimer acid composition contains less than 5 mole % of by-product elemental sulfur.
3. The method of claim 1 wherein the AOS dimer acid composition contains less than 2.5 mole % of by-product oxidizable components comprising hydrogen sulfide, sulfur dioxide, or mixtures thereof.

4. The method of claim 1 wherein the yield of AOS dimer acid is at least 85% of the theoretical amount.

5. The method of claim 1 wherein the AOS dimer acid composition has at least a 3% increase in sulfonic acid content compared with that of an AOS dimer acid composition prepared by the same process in the absence of any active removal of sulfur dioxide or hydrogen sulfide.

6. The method of claim 1 wherein step (b) is performed at a temperature within the range of 130° C. to 170° C.

7. The method of claim 1 wherein the alpha-olefin is a $C_5$ to $C_{50}$ linear or branched alpha-olefin.

8. The method of claim 1 further comprising removing sulfur dioxide from the mixture produced in step (a) prior to performing step (b) by digesting, vacuum stripping, gas purging, solvent-assisted stripping, heating, or a combination thereof.

9. A method which comprises:
   (a) sulfonating an alpha-olefin to produce a mixture comprising an alpha-olefin sulfonic acid (AOS acid) and sulfur dioxide;
   (b) removing sulfur dioxide from the mixture produced in step (a); and
   (c) heating the mixture from step (b) in a reactor at a temperature within the range of 110° C. to 200° C. to produce an AOS dimer acid composition;
   wherein the AOS dimer acid composition has at least a 30% decrease in the level of elemental sulfur when compared with that of an AOS dimer acid composition prepared by the same process in the absence of any active removal of sulfur dioxide.

10. The method of claim 9 wherein the AOS dimer acid composition contains less than 5 mole % of by-product elemental sulfur.

11. The method of claim 9 wherein the AOS dimer acid composition contains less than 2.5 mole % of by-product oxidizable components comprising hydrogen sulfide, sulfur dioxide, or mixtures thereof.

12. The method of claim 9 wherein the yield of AOS dimer acid is at least 85% of the theoretical amount.

13. The method of claim 9 wherein the AOS dimer acid composition has at least a 3% increase in sulfonic acid content compared with that of an AOS dimer acid composition prepared by the same process in the absence of any active removal of sulfur dioxide or hydrogen sulfide.

14. The method of claim 9 wherein step (c) is performed at a temperature within the range of 130° C. to 170° C.

15. The method of claim 9 wherein step (b) is performed by digesting, vacuum stripping, gas purging, solvent-assisted stripping, heating, or a combination thereof.

16. The method of claim 9 wherein the alpha-olefin is a $C_5$ to $C_{50}$ linear or branched alpha-olefin.

17. The method of claim 9 further comprising purging hydrogen sulfide and sulfur dioxide from the reactor during step (c).

18. A method which comprises:
   (a) sulfonating an alpha-olefin with sulfur trioxide to produce a mixture comprising an alpha-olefin sulfonic acid (AOS acid) and sulfur dioxide;
   (b) removing sulfur dioxide from the mixture produced in step (a) by digesting, vacuum stripping, gas purging, solvent-assisted stripping, heating, or a combination thereof; and
   (c) heating the mixture from step (b) in a reactor at a temperature within the range of 130° C. to 170° C. while purging sulfur dioxide and hydrogen sulfide from the reactor to produce an AOS dimer acid composition;
   wherein the AOS dimer acid composition has at least a 30% decrease in the level of elemental sulfur when compared with that of an AOS dimer composition prepared by the same process in the absence of any active removal of sulfur dioxide.

19. A AOS dimer acid composition made by the method of claim 1.

20. A salt prepared by neutralizing the AOS dimer acid composition of claim 19.

21. A AOS dimer acid composition made by the method of claim 9.

22. A salt prepared by neutralizing the AOS dimer acid composition of claim 21.

23. A AOS dimer acid composition made by the method of claim 18.

24. A salt prepared by neutralizing the AOS dimer acid composition of claim 23.

* * * * *